US007763058B2

(12) United States Patent
Sterenborg et al.

(10) Patent No.: US 7,763,058 B2
(45) Date of Patent: Jul. 27, 2010

(54) DEVICE AND METHOD FOR PHOTODYNAMIC THERAPY OF THE NASOPHARYNGEAL CAVITY

(76) Inventors: Dick Sterenborg, Faure straat 6, NL-2901 RC Capelle aan den Ijssel (NL); Bing Tan, Professor Tulpstraat 40, 1018HA Amsterdam (NL); Peter C. Levendag, Provenierssingel 5A, 3033 ED, Rotterdam (NL)

( * ) Notice: Subject to any disclaimer, the term of this patent is extended or adjusted under 35 U.S.C. 154(b) by 1167 days.

(21) Appl. No.: 11/272,328

(22) Filed: Nov. 10, 2005

(65) Prior Publication Data
US 2006/0111762 A1 May 25, 2006

Related U.S. Application Data

(60) Provisional application No. 60/629,765, filed on Nov. 20, 2004.

(51) Int. Cl.
*A61N 5/06* (2006.01)
(52) U.S. Cl. .......................... 607/88; 607/89; 128/898
(58) Field of Classification Search ...................... None
See application file for complete search history.

(56) References Cited

U.S. PATENT DOCUMENTS 3,664,330 A * 5/1972 Deutsch ..................... 600/104
4,269,192 A   5/1981 Matsuo
4,449,535 A   5/1984 Renault (Continued)

FOREIGN PATENT DOCUMENTS

EP      91201551.8      6/1991

(Continued)

OTHER PUBLICATIONS

Levendag, P.C., A new applicatgor design for endocavitary brackytherapy of cancer in the nasopharynx, Radiotherapy and Oncology, 1997, 95-98, Elsevier, Ireland.

*Primary Examiner*—Henry M Johnson, III
*Assistant Examiner*—Lynsey Crandall
(74) *Attorney, Agent, or Firm*—Bolesh J. Skutnik; BJ Associates (57) ABSTRACT

A device/system and method for the delivery of light to the nasopharyngeal cavity in a controlled and reproducible manner using at least one optical fiber having a linear diffusing tip, a spherical diffusing tip, or a bare cut end is disclosed. A positioning device may have one or two flexible guide tubes that are attached to a preformed shaped base that is introduced into the nasopharyngeal cavity to guide and position the optical fibers and/or detector(s). The optical fibers are enclosed within shielding tubes which are inserted into the guide tubes. The optical fibers may be further moved within the shielding tube so as to adjust the amount of output light. Also included within the guide tube is a light detector that monitors, detects, and measures the delivery of fluence rates to pre-determined locations in the nasopharyngeal cavity. The detector may also be enclosed within a separate tube within the guide tube. The inventive device/system also has a means of shielding preselected areas of the nasopharyngeal cavity or adjacent tissues from the light delivered by the optical fibers. The system of the present invention uses a control unit and preselected treatment parameters to monitor, regulate, and display laser output and fluence rates at preselected locations in the nasopharyngeal cavity during PDT treatment.

7 Claims, 10 Drawing Sheets

U.S. PATENT DOCUMENTS

| | | | |
|---|---|---|---|
| 4,576,168 A * | 3/1986 | Jalowayski | 606/198 |
| 4,998,930 A | 3/1991 | Lundahl | |
| 5,400,771 A * | 3/1995 | Pirak et al. | 600/109 |
| 5,445,608 A * | 8/1995 | Chen et al. | 604/20 |
| 5,590,660 A * | 1/1997 | MacAulay et al. | 600/478 |
| 5,803,080 A | 9/1998 | Freitag | |
| 5,814,041 A * | 9/1998 | Anderson et al. | 606/15 |
| 5,827,190 A * | 10/1998 | Palcic et al. | 600/476 |
| 5,997,571 A | 12/1999 | Farr et al. | |
| 6,513,527 B1 | 2/2003 | Abdel-Aziz | |
| 2004/0030368 A1 * | 2/2004 | Kemeny et al. | 607/88 |
| 2006/0271024 A1 * | 11/2006 | Gertner et al. | 606/2 |

FOREIGN PATENT DOCUMENTS

| | | |
|---|---|---|
| GB | 2057886 | 8/1980 |

* cited by examiner

FIG. 9

DEVICE AND METHOD FOR PHOTODYNAMIC THERAPY OF THE NASOPHARYNGEAL CAVITY

DOMESTIC PRIORITY UNDER 35 USC 119(e)

This application claims the benefit of U.S. Provisional Application Ser. No. 60/629,765, filed Nov. 20, 2004, which is incorporated by reference herein.

BACKGROUND OF THE INVENTION

1. Field of the Invention

The present invention relates to the field of photodynamic therapy and, in particular, to a device and method for controlled delivery of light to the nasopharyngeal cavity for the treatment of cancer.

2. Information Disclosure Statement

Photodynamic therapy (PDT) is a minimally invasive, non-surgical treatment option for a variety of diseases, including cancer. PDT utilizes photosensitizing drugs and specific wavelengths of visible light to generate singlet oxygen, which in turn, induces oxidative damage in target tissues. The cumulative effects of oxidative damage, namely necrosis, apoptosis, and/or vascular collapse, result in the localized destruction of the target tissue. PDT treatment results in localized and specific tissue destruction, in part, because visible light has a tissue penetration range of between 2.0-6.0 mm. As a result, PDT treatment substantially reduces trauma to underlying, healthy tissues and organs. In light of its localized and selective biological effects, PDT is an attractive alternative to other tumour therapies, such as chemotherapy and radiotherapy, especially when targeting cancerous tissues in the nasopharynx.

Conventional treatment of nasopharyngeal cancer consists of different combinations of chemotherapy and radiotherapy dosing regimes, which require high dose and high-precision techniques such as brachytherapy and stereotactic radiotherapy. These techniques deliver a maximum possible radiation dose to the nasopharyngeal cavity to limit damage to critical tissues such as the spinal cord, the optic nerve and the optical chiasma. However, this treatment scheme is time-consuming, technically demanding, and very stressful to the patient. Conventional radiotherapy methods often cause permanent radiation damage and unpleasant, long-term side effects. For example, xerostomia (dry mouth) is the result of permanent radiation damage to the salivary glands. Moreover, because conventional techniques administer a maximum radiation dose to the nasopharyngeal area, repeat dosing of radiotherapeutics is not an option in the event of recurrence. For recurring disease, surgery is the only treatment method currently available but it is rarely curative and highly disfiguring.

For patients experiencing recurring disease in the nasopharynx post-radiotherapy, PDT would be an excellent alternative to surgery. Unlike conventional radiotherapy methods, PDT could provide effective treatment of superficial (surface) tumours without substantial risk to adjacent healthy tissues and organs. In addition, using PDT as a local booster could either supplement conventional radiotherapy or, in certain situations, completely supplant radiotherapy altogether.

For effective destruction of target tissues, PDT requires uniform irradiation of the diseased tissue in the proper amount. Consequently, light intensity and light dose are critical factors to the overall efficacy of PDT treatments. But, PDT treatment in the nasopharyngeal cavity is problematic for two reasons: (1) light scattering and (2) the irregular geometry of the nasopharyngeal cavity. These two factors hamper the consistent delivery of a therapeutically effective light dose to the target tissue, which reduces the overall efficacy of PDT treatment.

The interaction of light with biological tissue is a complicated process that changes with tissue type, fluence rate, delivered dose, and wavelength of light. The processes of reflection, scattering, and partial absorption, diffuses light as it penetrates into biological tissue. Light dosimetry in PDT treatments is complicated by the light-tissue interaction process, which effectively increases the local light fluence rates and causing target tissues to receive a light dose that is many times higher than the original incoming light alone.

In an effort to deliver more uniform irradiation in hollow cavities such as, the bladder, the oesophagus, the oral and thoracic cavities, and the bronchi, a few dedicated light delivery systems have been developed for PDT treatment at individual treatment sites. In particular, Farr et al, in U.S. Pat. No. 5,997,571, titled, Non-Occluding Phototherapy Probe Stabilizers," describe a device for PDT treatments within the bronchia of the lung or other lumens. These researchers teach a fiber optic apparatus with a series of "non-occluding expansion elements" that can be "activated to protrude from the catheter body and contact the lumen walls" for centering an optical fiber. The disclosed projection elements are either rigid or inflatable. This reference does not teach a device expressly dedicated to PDT treatment in the nasopharyngeal cavity, nor does the reference predict or teach the successful use of the disclosed apparatus in the nasopharynx.

Lundahl in U.S. Pat. No. 4,998,930, entitled, "Intracavity Laser Phototherapy Method," discloses another irradiation method especially suited for irradiating inside the human urinary bladder. Lundahl teaches a balloon catheter for centering a light source within the bladder prior to laser therapy. The disclosure further teaches a method of positioning a fiber optic light source in an irregularly shaped cavity that requires inflation of a balloon. Inflation of the balloon reshapes the cavity into a relatively uniform spherical shape thus allowing for uniform irradiation of tissue.

The Rotterdam Nasopharynx Applicator (RNA) developed by Levendag et al. for positioning catheters to deliver radioactive materials into the nasopharyngeal cavity in brachytherapy is discussed in Radiotherapy and Oncology, 1997; pp. 95-88. Specifically, the RNA was designed to accommodate the use of fractionated high dose radiation protocols on an out-patient basis. To accommodate the requirements of out-patient brachytherapy, the RNA was designed to remain in situ for the duration of the radiotherapy treatment which varies from 2 to 6 days. However, due to the particular nature and methods of radiation therapy, the RNA is not particularly suited for use in PDT treatment of the nasopharynx.

The above-described references disclose devices/methods optimized for the treatment of spatially straightforward cavities, i.e., closer to a spherical or a cylindrical shape. For spatially straightforward surfaces, the fluence rate distribution at any point on the irradiated surface can be accurately predicted by measuring the fluence rate at a few select points. However, the nasopharynx is more spatially complex than either the spherically shaped bladder or the cylindrically shaped bronchi. This spatial complexity makes extrapolating the fluence rate distribution at any point in the nasopharynx from a small number of point measurements problematic at best. Moreover, due to the irregular geometry of the nasopharyngeal cavity, irradiation methods and devices which are suitable for spherical or cylindrical cavities, do not offer stable and reproducible positioning in the nasopharynx together with uniform irradiation of nasopharyngeal target tissues. Thus, PDT treatments in the nasopharynx require a very different approach to choosing illumination parameters.

As discussed above, the main setback for photodynamic therapy in the nasopharynx is the lack of a convenient, reproducible and controlled method for delivering light to the nasopharyngeal cavity. Treatment within the nasopharyngeal cavity necessitates the identification of "at risk" tissue areas as well as the treatment target area, which are determined beforehand using MR images or CT scans. This process is similar to the Planning Risk Volume ("PRV") and Planning Target Volume ("PTV") concepts used in radiotherapy planning. Using prior clinical experience, the minimum dose for delivery to the PTV and maximum dose for the PRV is chosen. However, uniform irradiation is critical for preventing under-exposure of diseased areas, as this would lead to recurrence of the tumour. Equally important is to prevent over-exposure of healthy or delicate tissues whose damage would lead to serious complications for the patient. The uniform illumination of the nasopharyngeal cavity thus requires a specialized device for use in PDT treatment in this area.

The present device and method address this need.

OBJECTIVES AND BRIEF SUMMARY OF THE INVENTION

It is an object of the present invention to provide a device for the uniform delivery of light to the nasopharyngeal cavity in a controlled and reproducible manner.

It is another object of the invention is to provide for the effective PDT treatment of superficial tumors in the nasopharynx without substantial risk to adjacent or underlying tissues and organs.

It is still another object of the invention to provide a device and method for calculating and controlling PDT light dosimetry for target tissues located in irregularly-shaped and/or spatially complex body cavities, and more specifically, for target tissues in the nasopharyngeal cavity.

Briefly stated, the present invention provides a device/system and method for the delivery of light to the nasopharyngeal cavity in a controlled and reproducible manner using at least one optical fiber having a linear diffusing tip, a spherical diffusing tip, or a bare cut end. A positioning device may have one or two flexible guide tubes that are attached to a preformed shaped base that is introduced into the nasopharyngeal cavity to guide and position the optical fibers and/or detector(s). The optical fibers are enclosed within shielding tubes which are inserted into the guide tubes. The optical fibers may be further moved within the shielding tube so as to adjust the amount of output light. Also included within the guide tube is a light detector that monitors, detects, and measures the delivery of fluence rates to pre-determined locations in the nasopharyngeal cavity. The detector may also be enclosed within a separate tube within the guide tube. The inventive device/system also has a means of shielding pre-selected areas of the nasopharyngeal cavity or adjacent tissues from the light delivered by the optical fibers. The system of the present invention uses a control unit and preselected treatment parameters to monitor, regulate, and display laser output and fluence rates at preselected locations in the nasopharyngeal cavity during PDT treatment.

The above and other objects, features, and advantages of the present invention will become apparent from the following description read in conjunction with the accompanying drawings.

DETAILED DESCRIPTION OF PREFERRED EMBODIMENTS

The present invention generally provides a device and method for the delivery of light to the nasopharyngeal cavity in a controlled and reproducible manner. In addition, the present invention provides for a positioning means for the stable and reproducible positioning of optical fibers in irregularly shaped cavities for the delivery of uniform illumination. In a preferred embodiment the inventive positioning means provides for improved PDT treatment of disease in the nasopharynx. Finally, the present invention provides a system and method for delivering uniform illumination as well as controlling the manner and characteristics of illumination during PDT.

Figure 1A:
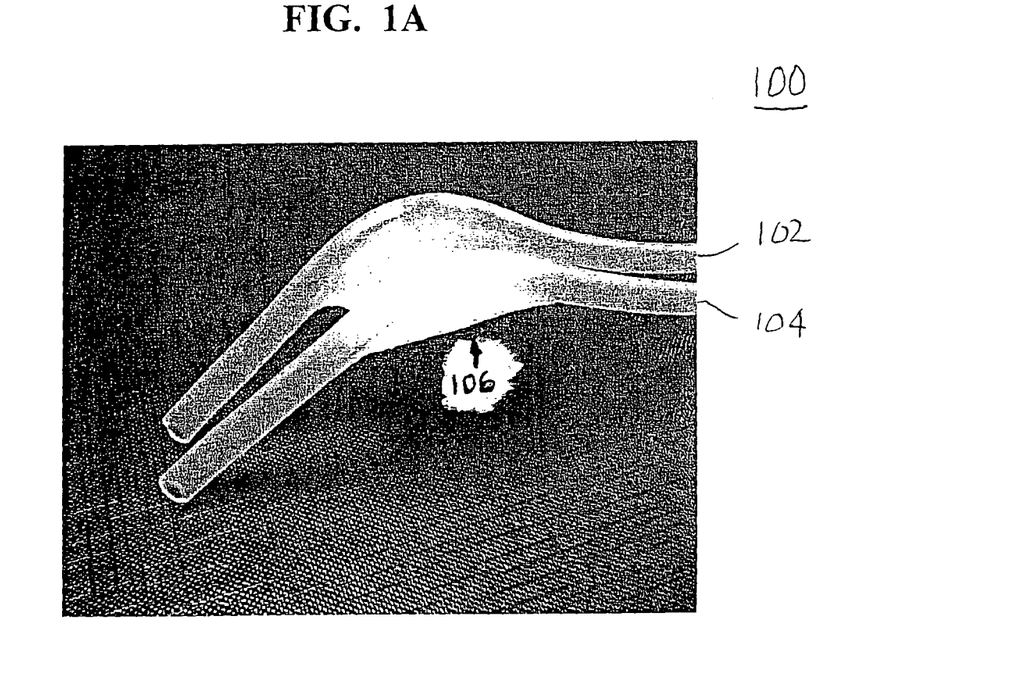
FIGS. 1A and 1B illustrate by different views the positioning means and guide tubes of the present invention.
Figure 4A:
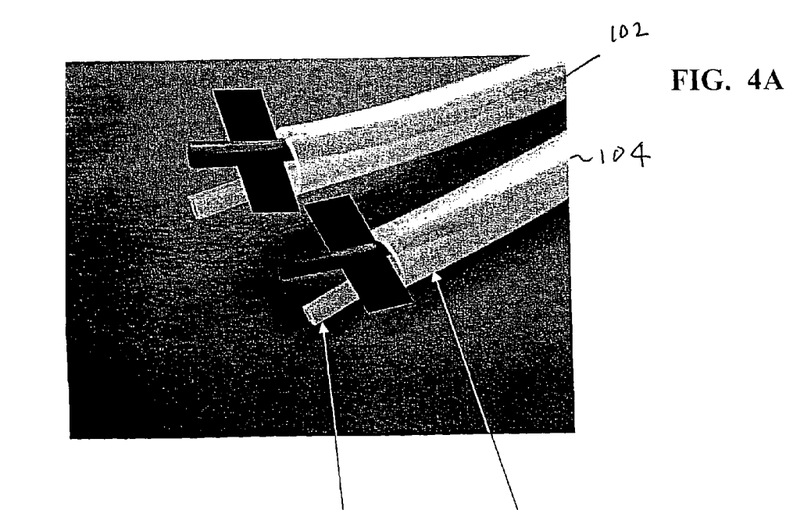
FIGS. 4A and 4B illustrate the detector with a shielding tube within the guide tube of the present invention.
Figure 4B:
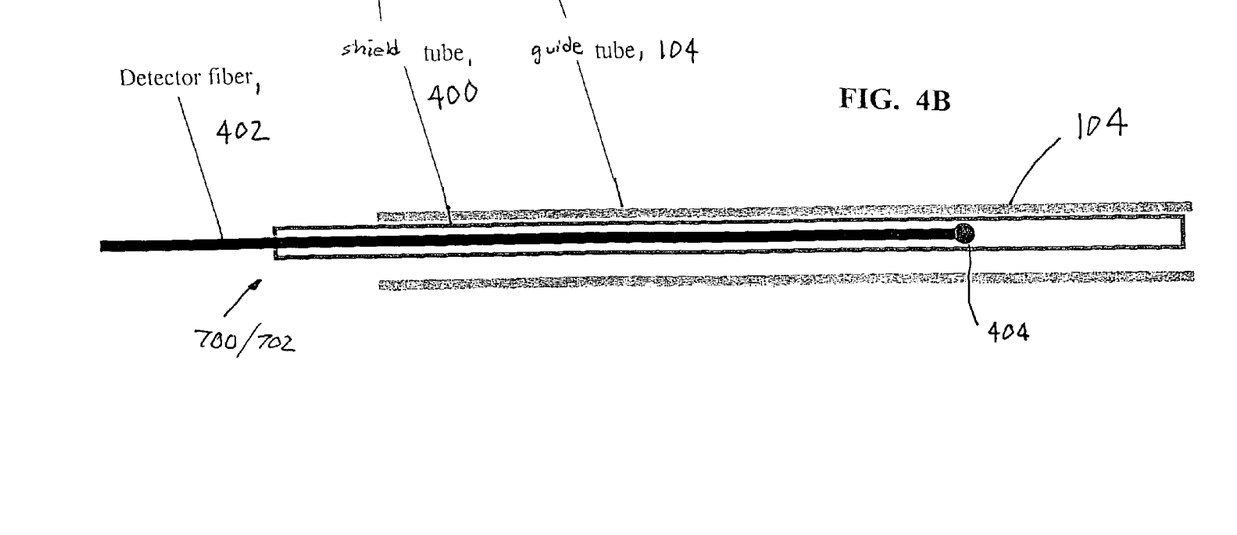
Figure 5:
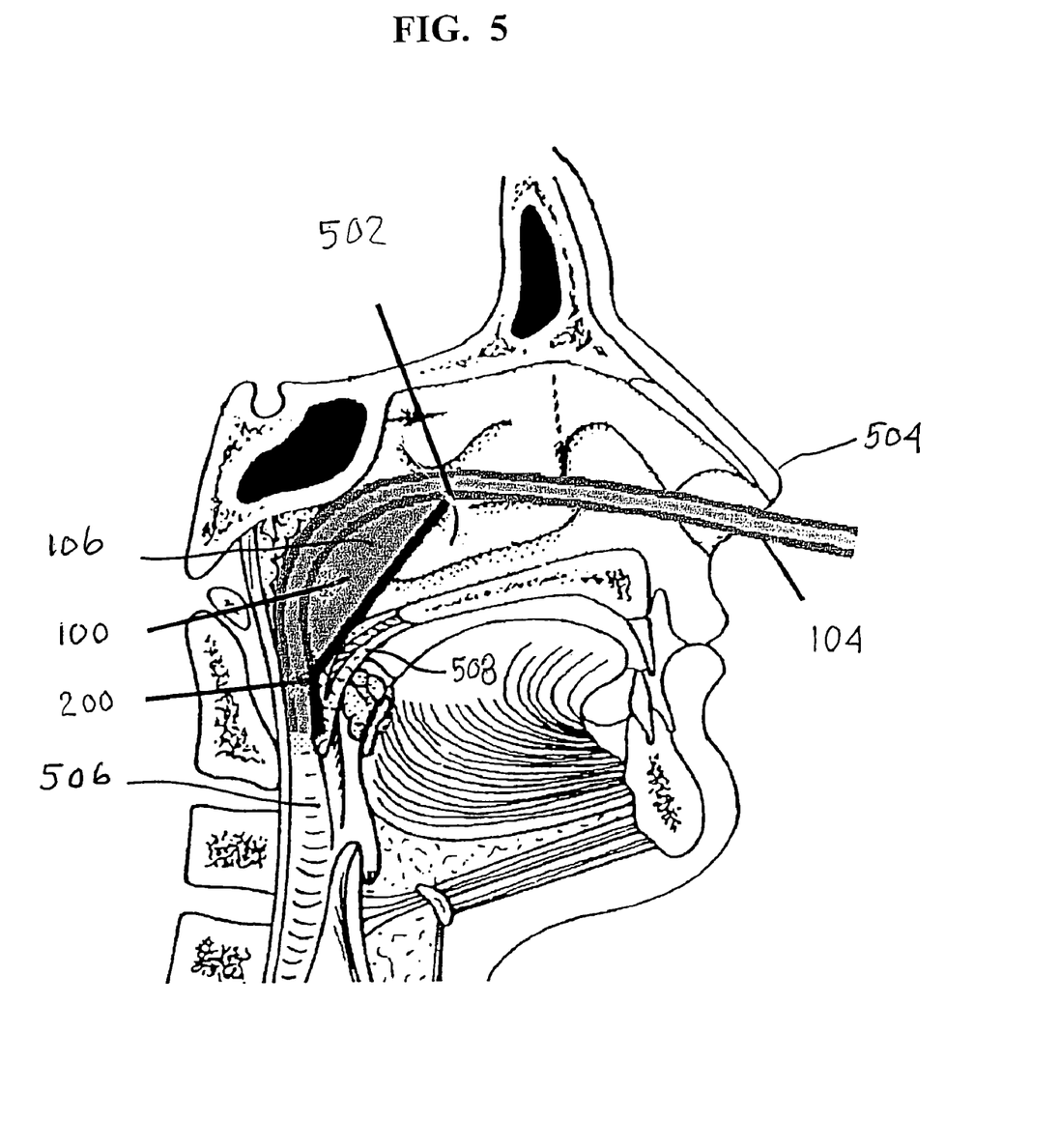
FIG. 5 illustrates the positioning of the inventive device within the nasopharyngeal cavity.

FIG. 1A illustrates the basic shape of positioning means 100 which guides the various optical fibers, FIG. 3, and control components, FIG. 4, into nasopharyngeal cavity 502, FIG. 5.

Figure 1B:
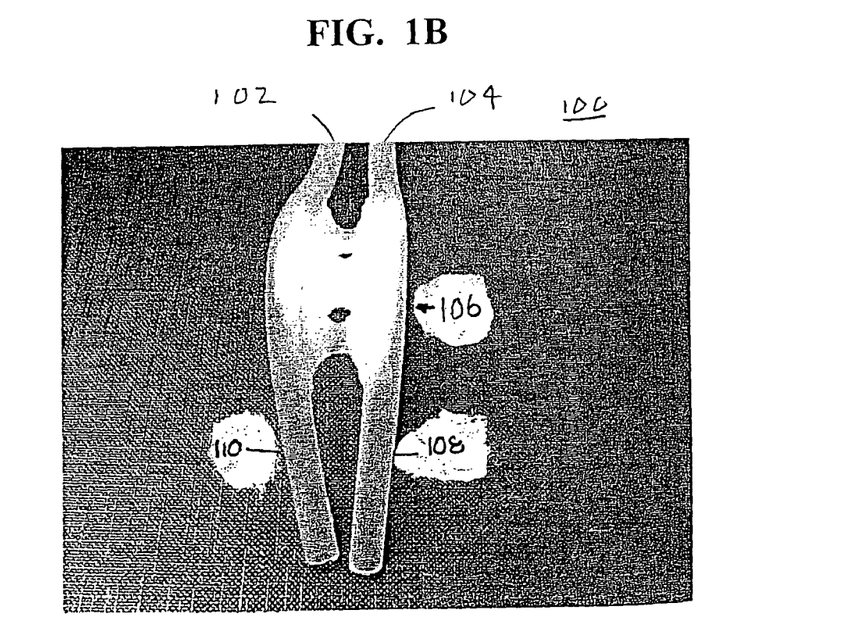

In this embodiment, positioning means 100 is comprised of at least one hollow guide tube 102 or preferably, two hollow guide tubes 102 and 104 which are removably connected by a base 106 and holds guide tubes 102 and 104 in a predetermined position with respect to each other and the base 106 in the area of the nasopharynx and oropharynx. As seen therein, from a side view, guide tubes 102 and 104 form an opened "V" and from the front view in FIG. 1B, guide tubes 102 and 104 form a closed "V" with the apex truncated so as to provide output sections 108 and 110. In this preferred embodiment, the configuration showed may be modified based upon the patient's characteristics as determined by physical and x-ray examinations and other tests. As will be shown below, the guide tubes 102 and 104 may be extended so that output sections 108 and 110 need not occur at the ends of guide tubes 102 and 104 but refer to the position of the output ends of the optical fibers therein. The ends of guide tubes 102 and 104 may fully extend and protrude from either the nose or the mouth or both thus providing several entrance means. It is therefore considered feasible that optical fibers or other components may be inserted into guide tubes 102 and 104 from either location, but preferably from the nose because of the shorter distance and few curves in the tubing. Base 106, being the positioning means, may be made of a soft plastic material being either non-transparent or transparent to the light. In the preferred embodiment, a transparent base 106 is shown.

Figures 2A, 2B, 2C:
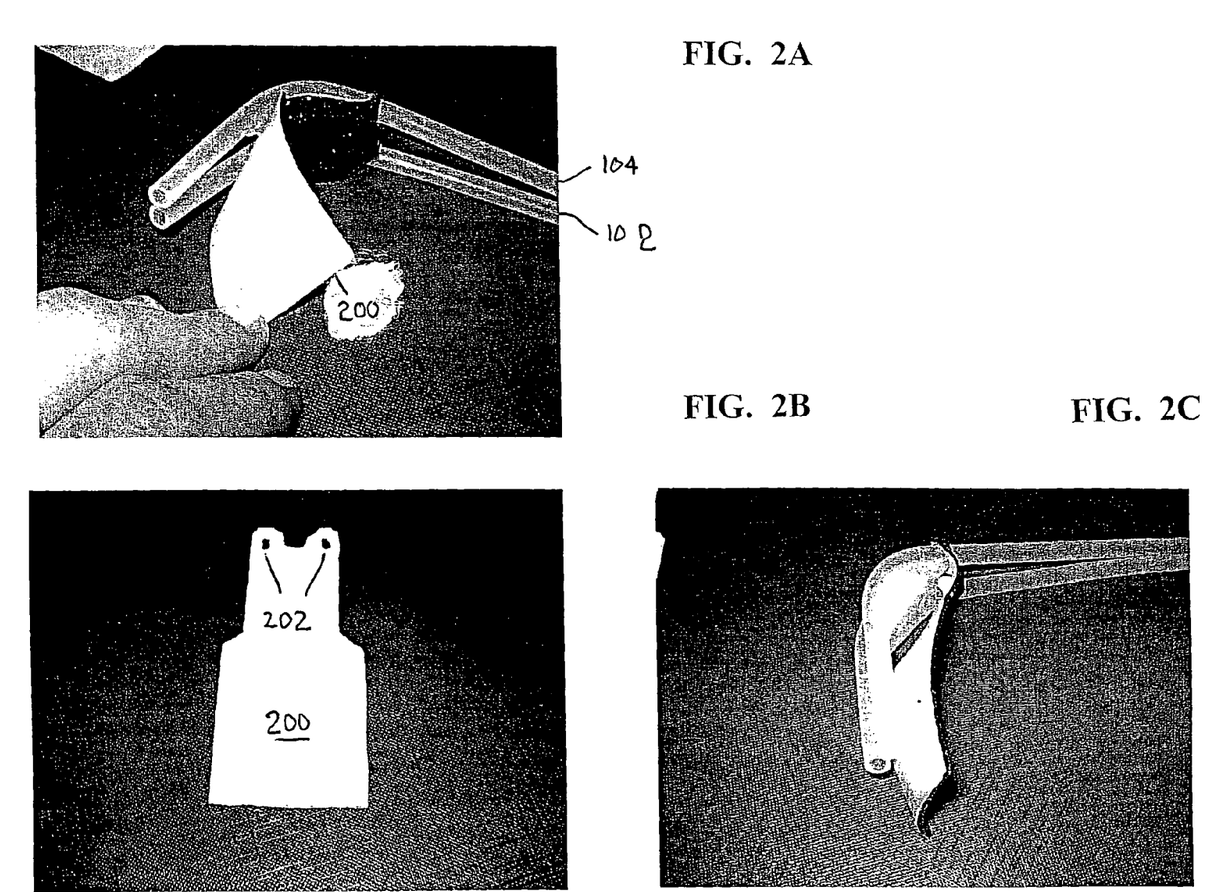
FIGS. 2A, 2B and 2C illustrate by different views the device of FIG. 1 with the means for blocking light attached thereon as used in the present invention.

Referring to FIGS. 2A, 2B and 2C, a light blocking means 200 is shown attached to guide tubes 102 and 104. Light blocking means 200 has the approximate shape of a stepped rectangular pad with a pair of holes 202 located at the upper end of the pad 200 as seen in FIG. 2B. The pad 200 as seen in FIG. 2 is located on the side of nasopharynx mucosa, away from the palate. As seen in FIG. 2, one side of pad 200 is reflective, being light colored therein, and enhances the amount of light away from the reflective side. The pad 200 may be on either side of the positioning means 100 as determined by the PRV (Planning Risk Volume). Further, pad 200 may be trimmed to fit a particular requirement so as to provide shielding of the underlying tissue from light emitted by the source optical fibers.

Figure 3A:
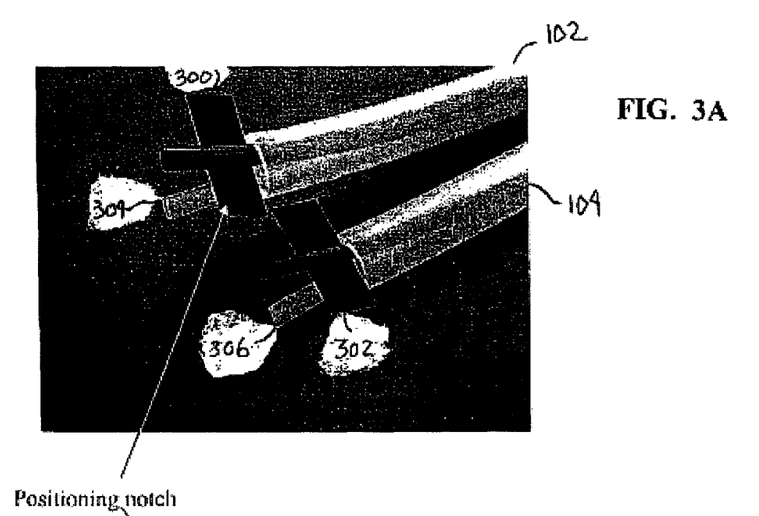
FIGS. 3A and 3B illustrate the optical fiber within a shielding tube within the guide tube of the present invention.
Figure 3B:
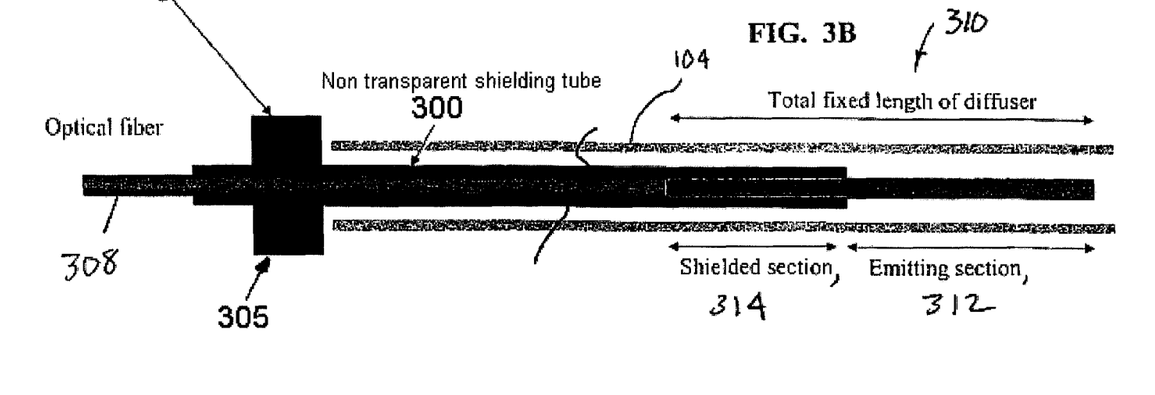
Figure 9:
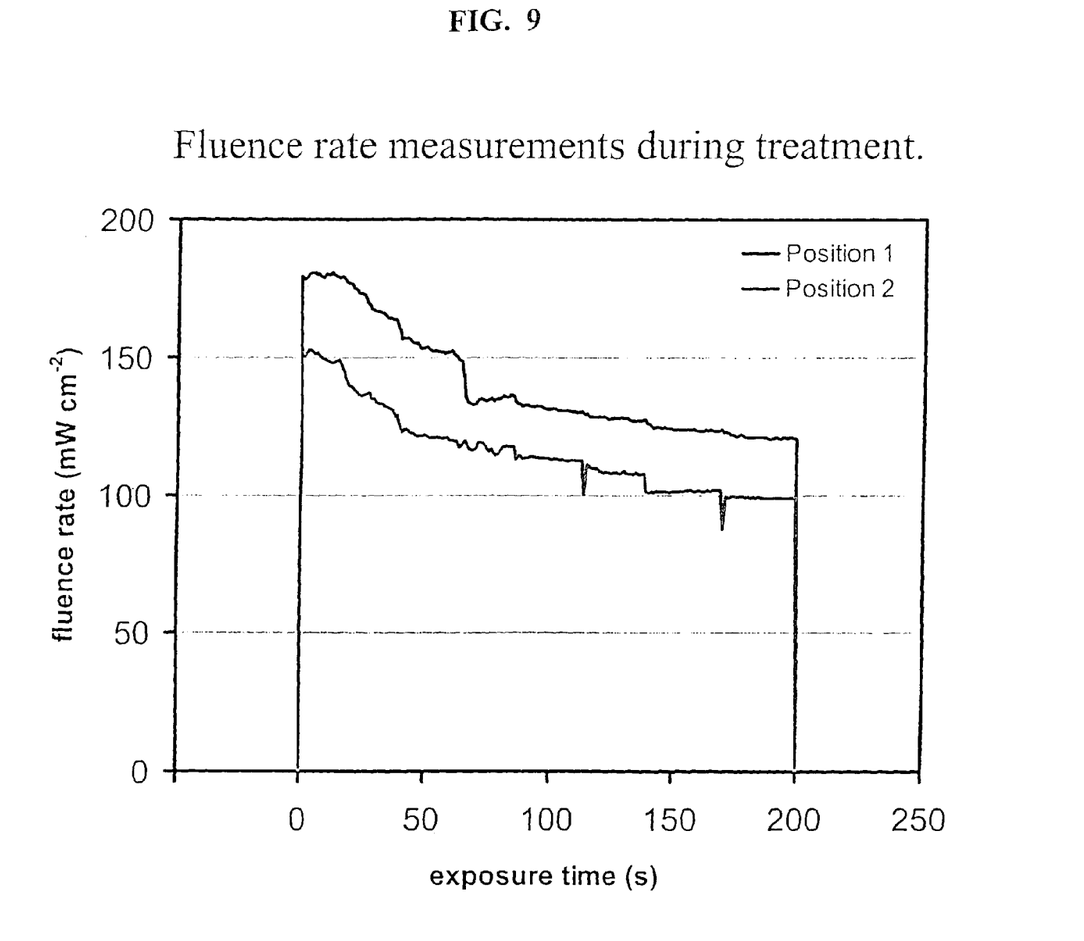
FIG. 9 is a graph showing different fluence rates for different positions of the optical fiber output end of the present invention.

FIG. 3A illustrates guide tubes 102 and 104 having therein optical fiber shielding tubes 300 and 302 with detector tubes 304 and 306. Each tube being a hollow flexible tube. FIG. 3B illustrates guide tube 104 with shielding tube 300. An optical fiber 308 is inserted into the shielding tube 300 with a linear diffuser 310. Other optical fiber output ends are feasible including siding firing. Attached to an appropriate position thereon, a positioning notch 305 determines the length of shielding tube 300 within guide tube 104. Linear diffuser 310 has two sections thereon which can change in length as determined by treatment parameters. As shown in FIG. 3B, an emitting section 312 of the diffuser 310 extends beyond shielding tube 300 which is non-transparent. Diffuser 310 has a shielded section 314 which is within the non-transparent shielding tube 300. By adjusting the length of the optical fiber within the shielding tube 300, different amounts of light can be applied to the treatment area. If the full diffuser length is outside of the shielding tube 300, a maximum is applied but in the configuration shown, a minimum of light is applied. FIG. 9 illustrates the fluence rates for these different positions.

FIG. 4A illustrates the use of a detector shield tube 400 within guide tube 104. Inside of the detector shield tube 400 is a detector fiber 402 having a detector element 404 that is appropriately positioned with guide tube 104 to measure, for example, fluence rate. Although the detector fiber 402 and the optical fiber 308 may be inserted into the guide tube without protective tubes, the preferred embodiment has detector fiber 402 within detector shield tube 400 and optical fiber 308 within shielding tube 300. The detector shield tube 400 and the optical fiber shielding tube 300 being separate tubes within the guide tube 104.

FIG. 5 illustrates the relative location of positioning means 100 after introduction into the nasopharynx cavity 502 of the respiratory system. Generally, positioning means 100 is introduced into the nasopharyngeal cavity 502 using a two step approach. First, after applying local anesthesia, two silicone guide tubes 102 and 104 are inserted into nose 504 until the ends of the tubes 102 and 104 are visible in the oropharynx 506. Next, using forceps, the now-visible ends are directed out through the mouth, while the distal ends remain protruding from the nose. Positioning means 100 of the present invention is then connected to the tubes exiting the mouth. Positioning means 100 is introduced into the nasopharyngeal cavity by pulling on the distal ends of tubes 102 and 104 protruding from nose 504. Using the above-described procedure, positioning means 100 enters through the mouth and is subsequently pulled into the nasopharyngeal cavity 502 until base 106 is in contact with nasal septum 508. Additionally before the positioning means 100 is attached, pad 200 is attached to the guide tubes 102 and 104 through the two holes 202.

Figure 6:
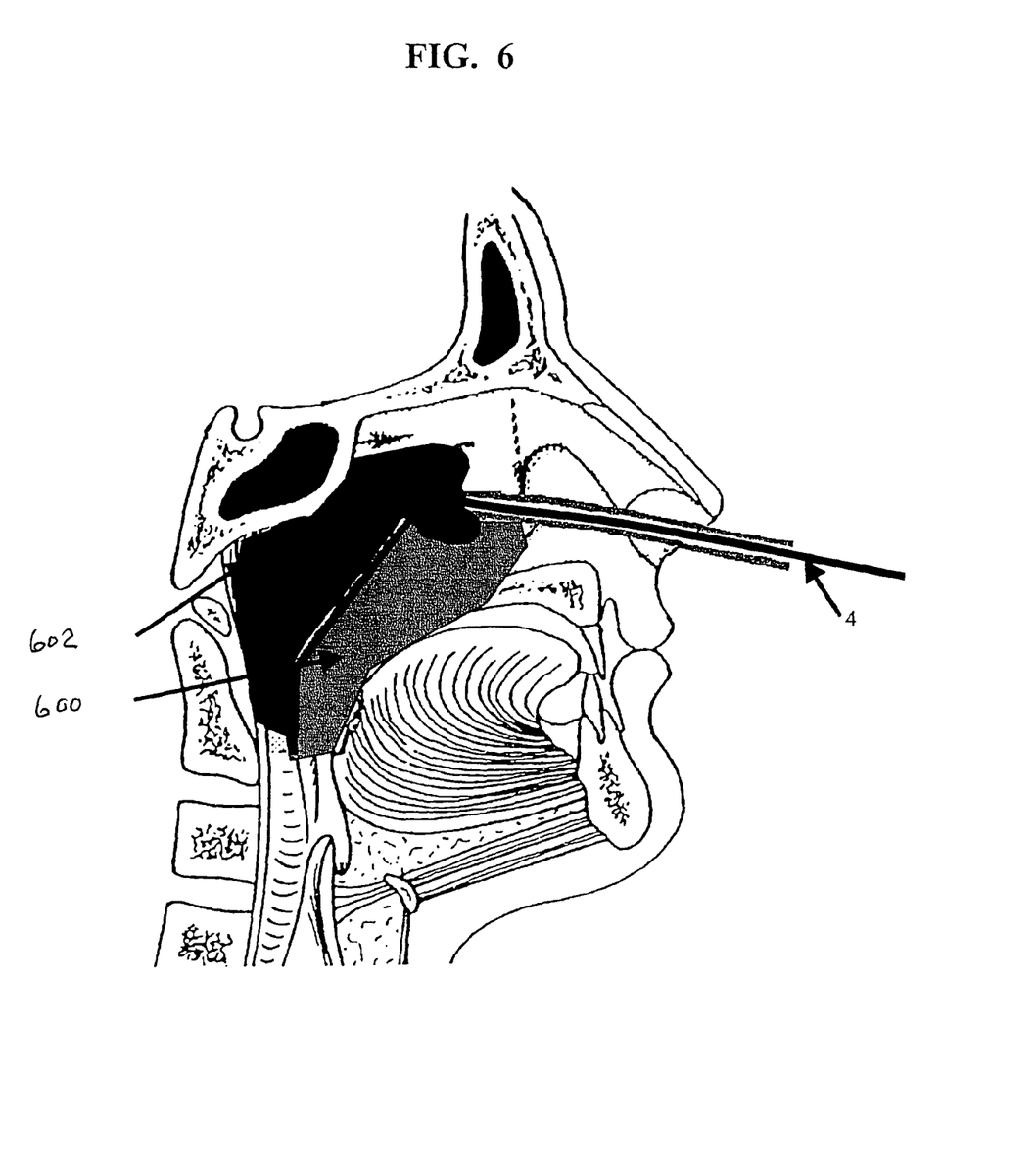
FIG. 6 illustrates a treatment situation using the inventive device within the nasopharyngeal cavity.
Figure 7A:
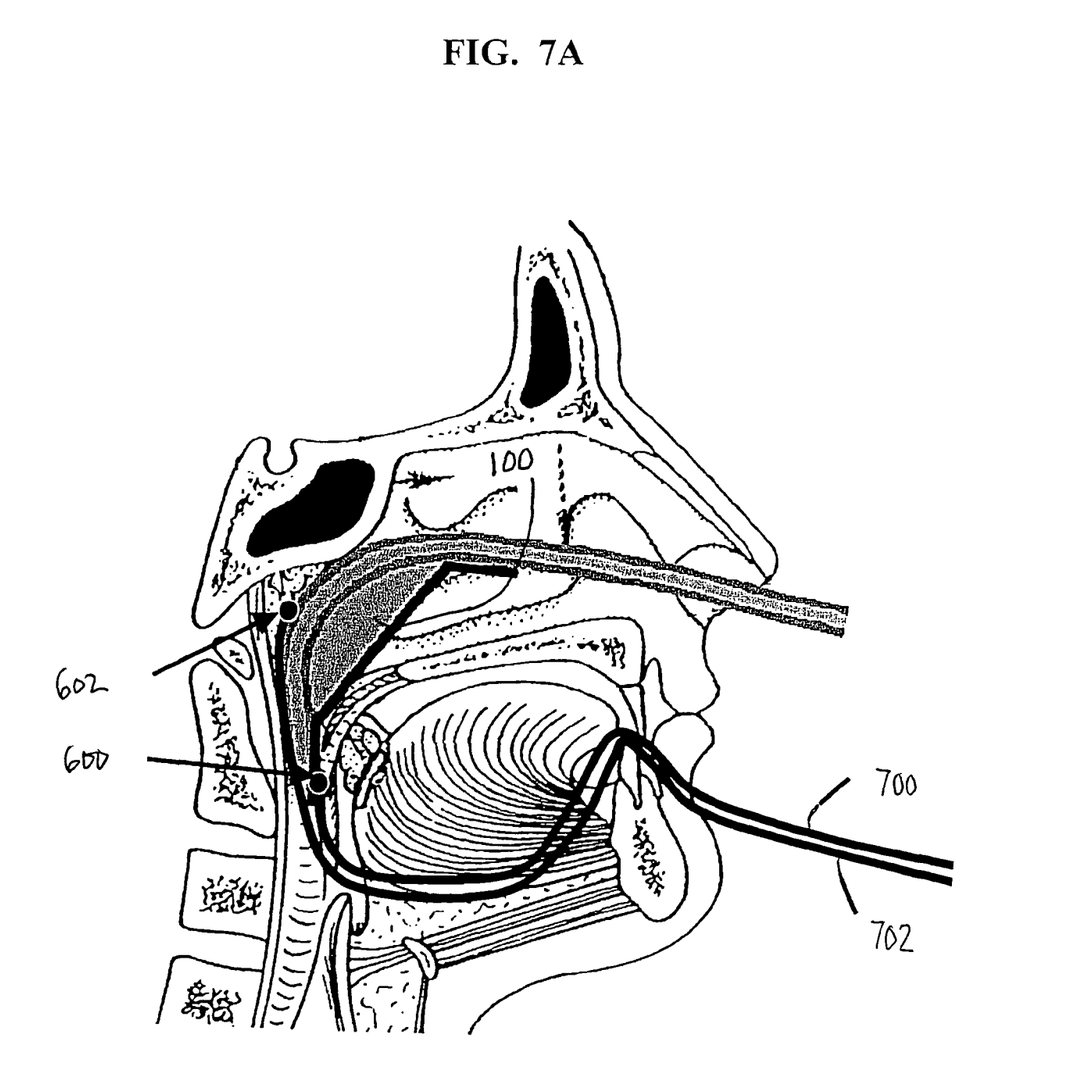
FIGS. 7A and 7B illustrate the different means for measuring and detecting light according to the present invention.
Figure 7B:
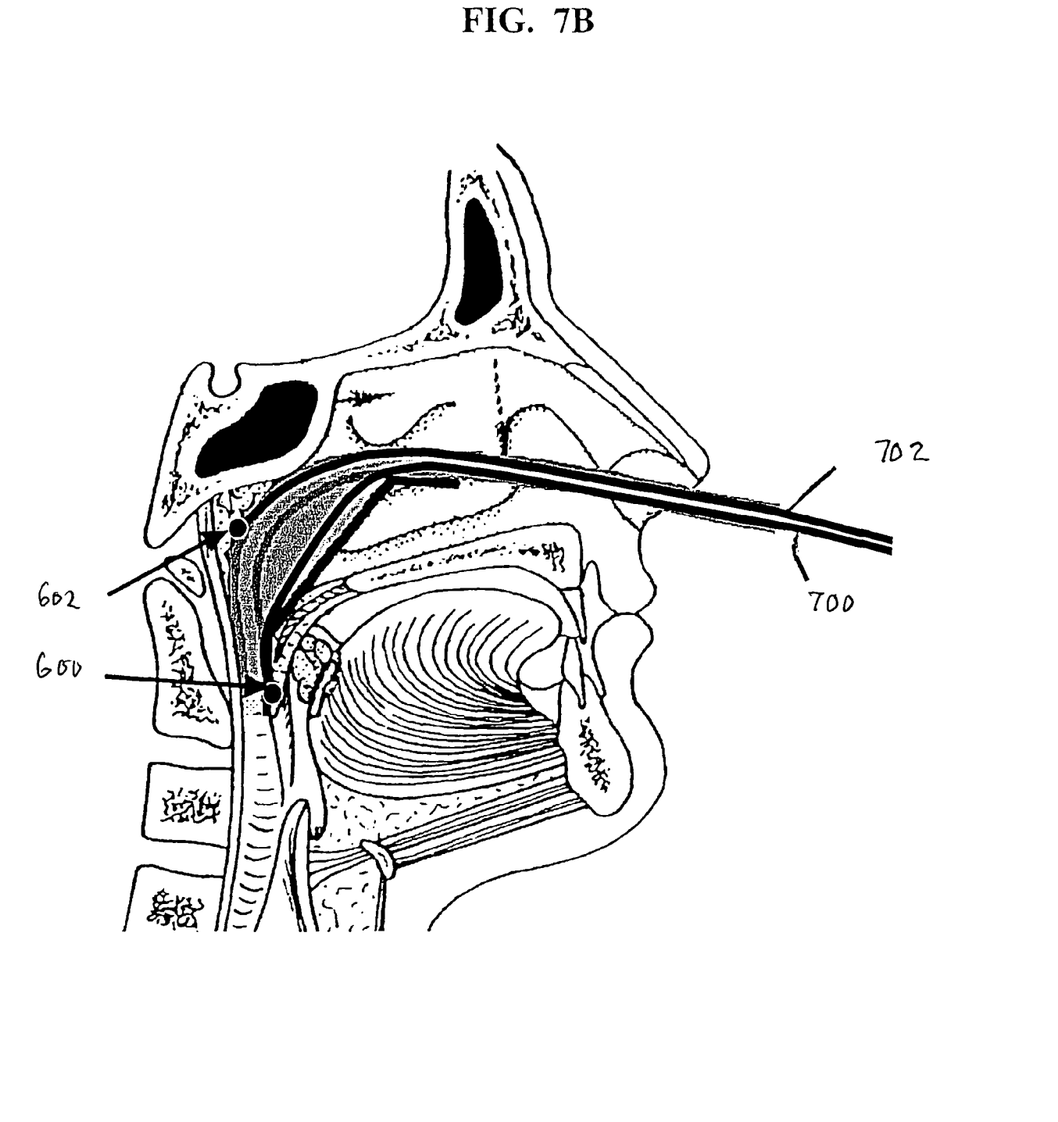

FIGS. 6, 7A and 7B illustrate various treatment situations in accord with the present invention. FIG. 6 illustrates an embodiment of the Planning Risk Volume, (PRV), 600 and the Planning Target Volume, (PTV), 602 which is located along the outer curve of the positioning means. PTV 602 is defined as that area of tissue within the nasopharynx being treated. PRV 600 would include all tissues, organs, etc., not with the area defined by PTV 602. FIGS. 7A and 7B illustrate the use of positioning means 100 together with various means for measuring and detecting light within the nasopharynx. Specifically, FIG. 7A illustrates an embodiment in which detecting means 700 and 702 are introduced via the mouth. In a preferred embodiment, detecting means 700 and 702 are positioned on PRV 600 and PTV 602, respectively. FIG. 7B shows another example of the positioning of detecting means 700 and 702 according to the present invention. In a preferred embodiment, detecting means are positioned on the PTV 602 and the PRV 600 using the positioning means 100 of the present invention. It should be understood that the detecting means 700 and 702 were previously shown in greater detail in FIGS. 4A and 4B and that detector fiber 402 was inserted into a detector shield tube 400 which was within the guide tube 104. This guide tube may be positioned through the nose or mouth or the detector fiber may be inserted without the guide tube from either location.

Figure 8:
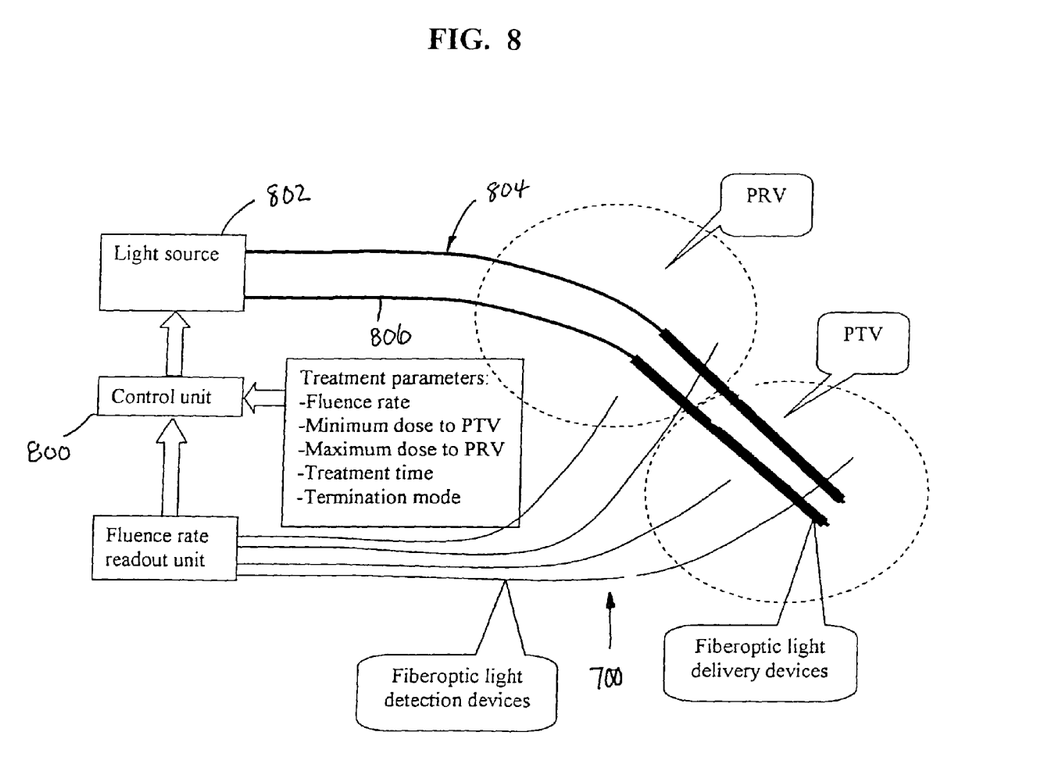
FIG. 8 is a schematic of the device and method of executing the treatment of the present invention.

Referring to FIG. 8, however, it is also preferred that the means for detecting and/or monitoring specific treatment parameters are also used to determine the operation of control unit 800. According to the present invention, it is preferred that these specific treatment parameters at least include: the desired fluence rate, and treatment time, the location/identity of the PTV and PRV, the minimum fluence to be delivered to the PTV, the maximum fluence to be delivered to the PRV and the choice which of the latter two is dominating the decision to terminate the treatment.

It is preferred that control unit 800 have means for controlling the optical power delivered to the fiberoptic light delivery devices according to measured fluence rates and calculated fluence rates so as to obtain a pre-selected fluence rate distribution. It is further preferred that the control unit have means for storing fluence rate data and for terminating illumination when the desired light dose has been delivered to one or more preselected locations.

In FIG. 8 control unit 800 monitors the signals from the fluence rate readout unit continuously. Control unit 800 collects, calculates, and analyzes fluence rate values measured by the detecting means 700 with respect to preselected treatment parameters to control the delivery of light from laser light source 802 to the different fiberoptic light-delivery devices 804 and 806. As a result, control unit 800 controls total output as well as the energy distribution over the different light delivery fibers. Control unit 800 also calculates and monitors the total fluence measured by the different detection fibers. Positioning means 100 positions the various fiberoptic light-delivery devices 804 and 806 and detection means in a stable and reproducible manner. The readout unit provides an on-going display of preselected treatment parameters or other relevant treatment data selected by the user.

Depending on the preselected treatment parameters and specific PTV and PRV geometry, it is preferred that control unit 800 has two possible modes of action when monitoring total fluence rates and that the operator chooses between these two modes before the treatment session begins.

In principle control unit 800 will monitor and display the delivered fluences and continue the treatment until the preset minimum fluence to the PTV has been reached. However, in the first mode of operation control unit 800 breaks off the treatment prior to this if the preset maximum fluence to the PRV has been reached. This mode of operation intends to limit the damage to critical tissues such as the optic nerve or the soft palate, even at the risk of not completely treating the tumor. The first mode of operation is typically used in palliative treatment. The second mode of operation aims at curative treatment. Here control unit 800 terminates the treatment only after the full preset fluence to the PTV has been delivered even if the delivered fluence to the PRV exceeds its maximum value.

In an alternate embodiment, when running in the second mode of operation, control unit 800 issues a warning message if the delivered fluence to the PRV has reached its preset maximum value and the delivered fluence to the PTV is not yet above its preset minimum value required for tumor eradication. In addition, the option is given to terminate the treatment instantly. While the warning is ignored the treatment continues as planned and terminates as soon as the delivered fluence to the PTV reaches its preset minimum value, accepting over-treatment in the PRV.

Having described preferred embodiments of the invention with reference to the accompanying drawing, it is to be understood that the invention is not limited to the precise embodiments, and that various changes and modifications may be effected therein by skilled in the art without departing from the scope or spirit of the invention as defined in the appended claims.

What is claimed is:

1. A method of providing photodynamic therapy to the nasopharyngeal tissue comprising the steps of:
    determining an area of treatment in the nasopharynx;
    administering appropriate photosensitizers to the patient;
    inserting at least one guide tube through the nose, through said nasopharynx, and through the oropharynx of the patient;
    directing the end of the at least one guide tube out through the mouth of the patient;
    attaching to said at least one guide tube a positioning base adapted to hold one or more guide tubes in a predetermined position within the nasopharyngeal cavity;
    introducing said positioning base into said nasopharynx;
    inserting into said at least one guide tube an optical fiber connected to a light source having a control unit;
    selecting treatment parameters available in said control unit;
    applying light from the light source through said optical fiber to activate the photosensitizers in said area of treatment until a predetermined treatment time is reached; and
    removing from said patient said positioning base, said guide tube, and said optical fiber after treatment.

2. A method for providing photodynamic therapy to the nasopharyngeal tissue according to claim 1 further including the step of attaching means to block light to said positioning means or said guide tube.

3. A method for providing photodynamic therapy to the nasopharyngeal tissue according to claim 1 further including the step of inserting into said guide tube at least one detector.

4. A method for providing photodynamic therapy to the nasopharyngeal tissue according to claim 1 wherein at least one of said preselected treatment parameters is selected from the group consisting of: identification of the Planning Target Volume (PTV), identification of the Planning Risk Volume (PRV), the minimum fluence to be delivered to the PTV, the maximum fluence to be delivered to the PRV, the optimum fluence rate in the PTV, and maximum treatment time.

5. A method for providing photodynamic therapy to the nasopharyngeal tissue according of claim 1 wherein said control unit monitors, calculates, and controls fluence rates at preselected locations using said predetermined treatment parameters to obtain a desired light dose.

6. A method for providing photodynamic therapy to the nasopharyngeal tissue according of claim 4 wherein said control unit controls the total output by comparing measured fluence rates with predefined fluence values for the PTV and the PRV.

7. A method for providing photodynamic therapy to the nasopharyngeal tissue according of claim 1 wherein said control unit has two possible selectable modes of action when monitoring total fluence rates.

* * * * *